United States Patent [19]

Cannon et al.

[11] 4,120,905

[45] Oct. 17, 1978

[54] REMOVAL OF NITROSATING AGENTS

[75] Inventors: William N. Cannon, Cumberland; Richard F. Eizember, Greenwood, both of Ind.

[73] Assignee: Eli Lilly and Company, Indianapolis, Ind.

[21] Appl. No.: 835,087

[22] Filed: Sep. 21, 1977

[51] Int. Cl.$^2$ ............................................. C07C 79/12
[52] U.S. Cl. ................................... 260/646; 260/701
[58] Field of Search ................................ 260/646, 701

[56] References Cited

U.S. PATENT DOCUMENTS 2,669,576   2/1954   Blomquist ............................ 260/467

OTHER PUBLICATIONS

Fridman, Russian Chemical Reviews, 40(1), pp. 34–50 (1971) (Eng.).
Cotton et al., Advanced Inorganic Chemistry, 1962, Interscience Publishers, pp. 254 to 260.
Mauch, Advanced Organic Chemistry: Reactions, Mechanisms and Structure, McGraw Hill, 1968, pp. 484 to 487.
Nenryo Oyobi Nensho, 1975, 42(8), pp. 745 to 755.

*Primary Examiner*—Leland A. Sebastian
*Attorney, Agent, or Firm*—Kathleen R. S. Page; Arthur R. Whale

[57] ABSTRACT

The present invention is directed to a process for removing nitrosating agents from 1-chloro-2,6-dinitro-4-(trifluoromethyl)benzene.

10 Claims, No Drawings

REMOVAL OF NITROSATING AGENTS

BACKGROUND OF THE INVENTION

The compound 1-chloro-2,6-dinitro-4-(trifluoromethyl)benzene:

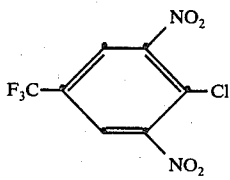

is the precursor to numerous dinitroaniline herbicides, such as trifluralin, benefin, ethalfluralin, fluchloralin, and profluralin. The compound is aminated

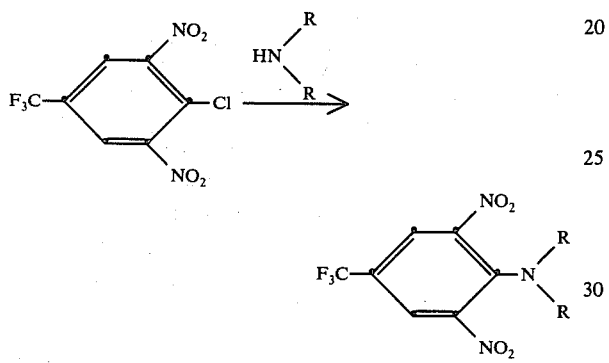

to obtain the various dinitroanilines.

Because the advent of a new analytical device known as a thermal energy analyzer (TEA), it is now possible to analyze for the nitroso group at concentrations as low as 0.02 ppm — much lower than prior analytical techniques. Analysis of various dinitroanilines by the TEA reveals that some of the dinitroanilines contain very small amounts of nitrosamine. Certain nitrosamine compounds have been shown to be carcinogenic in animals. Therefore, it is desirable to minimize nitrosamine concentrations in the dinitroanilines.

The present process provides a unique method of lowering nitrosamine concentrations in the dinitroanilines. The precursor compound, 1-chloro-2,6-dinitro-4-(trifluoromethyl)benzene, is generally prepared by nitration of the corresponding 1-chloro-4-(trifluoromethyl)benzene:

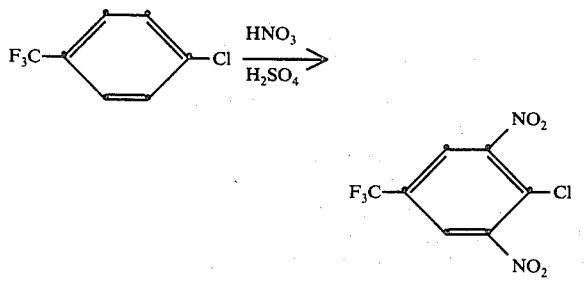

It is now believed that the 1-chloro-2,6-dinitro-4-(trifluoromethyl)benzene, as thus produced, contains as impurities small amounts of nitrosating agents, including substances which can react to form the actual nitrosating species. It is conjectured that the nitrosating agents form nitrosamines on exposure to the amine employed in the subsequent amination step.

By lowering the concentration of nitrosating agents in 1-chloro-2,6-dinitro-4-(trifluoromethyl)benzene, the present process also reduces nitrosamine concentration in any ensuing dinitroaniline product.

BRIEF SUMMARY

The present invention is directed to a process for lowering the concentration of nitrosating agents in 1-chloro-2,6-dinitro-4-(trifluoromethyl)benzene, which comprises (1) bubbling a gas which is non-reactive with 1-chloro-2,6-dinitro-4-(trifluoromethyl)benzene through a mixture of (a) 1-chloro-2,6-dinitro-4-(trifluoromethyl)benzene containing nitrosating agents and (b) an aqueous solution of a base which is
  (a) sodium carbonate,
  (b) potassium carbonate,
  (c) sodium hydroxide, or
  (d) potassium hydroxide
at a temperature of about 50°–100° C., until the concentration of nitrosating agents is lowered; or (2) contacting 1-chloro-2,6-dinitro-4-(trifluoromethyl)benzene containing nitrosating agents with an aqueous solution of a base which is
  (a) sodium carbonate,
  (b) potassium carbonate,
  (c) sodium hydroxide, or
  (d) potassium hydroxide,
at a temperature of about 50°–100° C., separating the once-treated 1-chloro-2,6-dinitro-4-(trifluoromethyl)-benzene, and thereafter bubbling a gas which is non-reactive with 1-chloro-2,6-dinitro-4-(trifluoromethyl)-benzene through an aqueous mixture of the once-treated 1-chloro-2,6-dinitro-4-(trifluoromethyl)-benzene, at a temperature of 50°–100° C., whereby there is obtained 1-chloro-2,6-dinitro-4-(trifluoromethyl)benzene characterized by a lowered concentration of nitrosating agents.

The present process can be carried out in several ways. The treatment with base can be simultaneous with the treatment with gas. Alternatively, the treatment with base can be carried out first, followed by treatment with gas, in either water or an aqueous solution of additional base. A plurality of base treatments can be used, so long as a treatment with gas follows a treatment with base.

In a preferred embodiment, the base is sodium carbonate, the gas is air, and aeration is carried out simultaneously with the base treatment. In another preferred embodiment, a first treatment with only aqueous sodium carbonate solution is followed by a combined second treatment with both aqueous sodium carbonate solution and aeration.

DETAILED DESCRIPTION

In the present process, the 1-chloro-2,6-dinitro-4-trifluoromethyl)benzene containing nitrosating agents is treated in a liquid phase. The compound, when pure, melts at about 52° C. Generally, treatment temperatures of 50°–100° C. are suitable. Preferred temperatures are 60°–70° C.

The amount of base employed is not critical, so long as the amount is effective to lower the concentration of nitrosating agents. In general, sufficient base should be utilized to provide an end pH of from about 8 to about 11. Where sequential treatments are conducted, less base is necessary in the aeration treatment, or the aeration treatment can be carried out in only water; but the end pH should be in the same range of from about 8 to about 11.

The gas to be employed is not critical, so long as it is non-reactive with the 1-chloro-2,6-dinitro-4-(trifluoromethyl)benzene. Air, nitrogen, and carbon dioxide have been employed with satisfactory results. The rate of introduction is not critical, either, so long as the total amount of gas supplied is effective to lower the concentration of nitrosating agents. On a laboratory scale, aeration at a rate of 450 ml/min. per 100 grams of 1-chloro-2,6-dinitro-4-(trifluoromethyl)benzene, over a treatment period of 30 minutes, has provided good reduction of nitrosating agents. On a larger scale, aeration at a rate of 16 to 25 ml/min. per 100 grams of 1-chloro-2,6-dinitro-4-(trifluoromethyl)-benzene, during a treatment period of 30 minutes to 6 hours, has provided good reduction of nitrosating agents. It appears that a larger volume of gas may be required for a single treatment with no separation.

The progress of the present process will depend on a number of factors, including the original concentration of nitrosating agents in the 1-chloro-2,6-dinitro-4-(trifluoromethyl)benzene, whether one or more than one treatment is carried out, the amount(s) of base used, the volume of gas used, and other factors. Although there is no convenient technique for assaying nitrosating agents in 1-chloro-2,6-dinitro-4-(trilouormethyl)benzene, the compound can readily be aminated to one of the dinitroanilines, which can then be analyzed for nitrosamine content by standard procedures. In general, treatment times of 30 minutes to 2 hours are adequate. Nitrosamine concentration in the final dinitroaniline products in generally lowered to below 20 ppm by the present process (compared to concentrations in the general range of 100-300 ppm with untreated 1-chloro-2,6-dinitro-4-(trifluoromethyl)benzene).

Preferred conditions to date have varied with the scale of reaction. On a laboratory scale, Examples 2 and 3 below represent the best practice. On a larger scale, the best procedure is represented by Example 7, below; however, a shorter second treatment time of only 1 hour is essentially as satisfactory in terms of lowering nitrosating agents, while shortening overall treatment times.

In all embodiments, it has been found preferable that the 1-chloro-2,6-dinitro-4-(trifluoromethyl)benzene be well separated from the aqueous portion of the treatment mixture prior to amination.

In the following examples, analyses for nitrosamine were carried out by standard procedures (Gas Chromatography-Flame Ionization Detection ("GC-FID"), Gas Chromatography-Mass Spectroscopy ("GC-MS"), or Gas Chromatography-Thermal Energy Analysis ("GC-TEA")).

EXAMPLE 1: SINGLE, SIMULTANEOUS TREATMENT

Sodium carbonate (6.25 grams) was mixed with water (20 ml.) and 1-chloro-2,6-dinitro-4-(trifluoromethyl)-benzene (28.9 grams) at a temperature of about 70° C. was added. The mixture was stirred vigorously at about 70° C. and sparged with air, for about an hour.

The 1-chloro-2,6-dinitro-4-(trifluoromethyl)-benzene was aminated, without separation, with di-n-propylamine. A sample of the N,N-di-n-propyl-2,6-dinitro-4-(trifluoromethyl)aniline product was found to contain 8 ppm of N-nitroso-N-,N-di-n-propylamine.

EXAMPLES 2 & 3: SINGLE, SIMULTANEOUS TREATMENT

A sample of 1-chloro-2,6-dinitro-4-(trifluoromethyl)-benzene (34.7 grams) was heated to about 70° C. and added to a solution of sodium carbonate (7.4 grams) in water (24 ml.). The mixture was heated to 70° C. and air was bubbled through for 1 hour.

The 1-chloro-2,6-dinitro-4-(trifluoromethyl)-benzene was aminated, without separation, with di-n-propylamine. The N,N-di-n-propyl-2,6-dinitro-4-(trifluoromethyl)aniline product was found to contain 3 ppm of N-nitroso-N,N-di-n-propylamine (compared to 494 ppm in a control prepared from a sample of 1-chloro-2,6-dinitro-4-(trifluoromethyl)benzene held at about 70° C. for ½ hour, as the only treatment).

In another treatment conducted in accordance with the same procedures, except that the 1-chloro-2,6-dinitro-4-(trifluoromethyl)benzene was isolated prior to amination, the ensuing N,N-di-n-propyl-2,6-dinitro-4-(trifluoromethyl)-aniline product was found to contain 1 ppm of N-nitroso-N,N-di-n-propylamine.

EXAMPLES 4-6: SINGLE, SIMULTANEOUS TREATMENT, VARYING IDENTITY OF GAS

A series of three experiments was conducted utilizing, as the gas, air, $N_2$, or $CO_2$.

Sodium carbonate (7.4 grams) was slurried in water (24 ml) and 1-chloro-2,6-dinitro-4-(trifluoromethyl)benzene (35 grams) at a temperature of about 70° C. was added. The mixture was maintained at about 70° C. and the respective gas was bubbled through for 2 hours.

Each treated lot of 1-chloro-2,6-dinitro-4-(trifluoromethyl)benzene was aminated, without separation, with di-n-propylamine. The ensuing N,N-di-n-propyl-2,6-dinitro-4-(trifluoromethyl)aniline product was analyzed for N-nitroso-N,N-di-n-propylamine. The results were as follows:

| Gas employed in Treatment | Concentration of N-nitroso-N,N-di-n-propylamine |
| --- | --- |
| air | 3-15* ppm |
| $N_2$ | 3-15* ppm |
| $CO_2$ | 9 ppm |

*in each instance, the peak was partially obscured by another peak, and the concentration could not be read with the usual degree of accuracy.

EXAMPLE 7: TWO TREATMENTS, AERATION IN SECOND TREATMENT

Sodium carbonate (500 kg) was added to water (4000 liters) and heated to a temperature of 65° C., and the solution was stirred at about 65° C. for 30 minutes. A total of 5790 kg. of 1-chloro-2,6-dinitro-4-(trifluoromethyl)-benzene at a temperature of about 70° C. was added. With agitation, the mixture was adjusted to a temperature of 65°-70° C.; agitation was continued for 30 minutes. The mixture was then allowed to separate 45 minutes at 68°-70° C., into two phases.

Separately, 100 kg of sodium carbonate was dissolved in 4000 liters of water and the solution heated to 60° C. The product layer from the first procedure was added, and the mixture was stirred at 60°-70° C. and aerated at 52 cubic feet per minute, for 2 hours. The 1-chloro-2,6-dinitro-4-trifluoromethyl)benzene was then separated.

Various portions of the 1-chloro-2,6-dinitro-4-(trifluoromethyl)benzene (treated as described above) were aminated with N-n-butyl-N-ethylamine, to produce N-n-butyl-N-ethyl-2,6-dinitro-4-(trifluoromethyl)aniline, or with N-ethyl-N-methallylamine, to produce N-ethyl-N-methallyl-2,6-dinitro-4-(trifluoromethyl)aniline. Each product was analyzed for nitrosamine content. The N-n-butyl-N-ethyl-2,6-dinitro-4-(trifluoromethyl)aniline was found to contain 7 or 20 ppm of N-nitroso-N-n-butyl-N-ethylamine (two different analytical laboratories) and the N-ethyl-N-methallyl-2,6-dinitro-4-(trifluoromethyl)aniline was found to contain 16 ppm of N-nitroso-N-ethyl-N-methallylamine.

EXAMPLE 8: FOUR TREATMENTS, AERATION IN THIRD TREATMENT

Sodium carbonate (60 grams) was added with agitation of water (475 ml) and the solution heated to 70° C. A 1046 gram portion of a lot of 1-chloro-2,6-dinitro-4-(trifluoromethyl)benzene which had previously been treated with an aqueous sodium carbonate solution at about 70° C. for 30 minutes was added at a temperature of about 70° C., and the mixture was stirred at about 70° C. for 30 minutes. The 1-chloro-2,6-dinitro-4-(trifluoromethyl)benzene was then separated.

Sodium carbonate (12 grams) was added with agitation to water (475 ml) and the solution heated to 70° C. The 1-chloro-2,6-dinitro-4-(trifluoromethyl)benzene from the prior procedure was added and the mixture was aerated at 70° C. for 2 hours. The 1-chloro-2,6-dinitro-4-(trifluoromethyl)benzene was separated.

Sodium carbonate (12 grams) was added with agitation to water (475 ml) and the mixture heated to 70° C. The 1-chloro-2,6-dinitro-4-(trifluoromethyl)benzene from the prior procedure was added and the mixture stirred at about 70° C. for 30 minutes. The 1-chloro-2,6-dinitro-4-(trifluoromethyl)benzene was then separated.

Each of two samples of the treated 1-chloro-2,6-dinitro-4-(trifluoromethyl)benzene was reacted with di-n-propylamine, yielding N,N-di-n-propyl-2,6-dinitro-4-(trifluoromethyl)aniline. Each product was analyzed for N-nitroso-N,N-di-n-propylamine by each of three different analytical laboratories (twice, in the GC-TEA method). The results were as follows.

|  | GC-FID | GC-FID | GC-TEA |
| --- | --- | --- | --- |
| Sample 1 | 12 ppm | 5 ppm | 5 and 7 ppm |
| Sample 2 | 11 ppm | 4.0 ppm | 6 and 10 ppm |

EXAMPLES 9–12: TWO TREATMENTS, AERATION IN SECOND, VARYING AMOUNT OF SODIUM CARBONATE

A series of four reactions was conducted, varying the amount of sodium carbonate in each of the two treatments.

In the first treatment, three procedures were used.
(A) Water (300 ml) was heated to 70° C. and 483 grams of 1-chloro-2,6-dinitro-4-(trifluoromethyl)-benzene at a temperature of about 70° C. was added. The mixture was agitated vigorously at about 70° C. for 30 minutes, and the 1-chloro-2,6-dinitro-4-(trifluoromethyl)-benzene was separated.
(B) Same as (A) except that only 150 ml of water and 242 grams of 1-chloro-2,6-dinitro-4-(trifluoromethyl)benzene were used and that sodium carbonate (4.16 grams) was added.
(C) Same as (B) except that the amount of sodium carbonate was 20.81 grams.

Thereafter each sample was treated a second time, in the following procedures. Water (150 ml) (an aqueous solution of sodium carbonate in 150 ml of water, in the instance of those treatments employing sodium carbonate) was heated to 70° C. and 1-chloro-2,6-dinitro-4-(trifluoromethyl)benzene (209 grams), at a temperature of about 70° C., was added. The mixture was aerated, with vigorous agitation, for 2 hours at about 70° C. The 1-chloro-2,6-dinitro-4-(trifluoromethyl)benzene was separated.

Samples of the 1-chloro-2,6-dinitro-4-(trifluoromethyl)benzene was aminated with di-n-propylamine and the final N,N-di-n-propyl-2,6-dinitro-4-(trifluoromethyl)aniline product analyzed for N-nitroso-N,N-di-n-propylamine.

| First Treatment | Second Treatment | Concentration of N-nitroso-N,N-di-n-propylamine |
| --- | --- | --- |
| no carbonate | no carbonate | 244 ppm |
| no carbonate | 4.16 grams of sodium carbonate | 146 ppm |
| 4.16 grams of sodium carbonate | 4.16 grams of sodium carbonate | 29 ppm |
| 20.81 grams of sodium carbonate | 4.16 grams of sodium carbonate | 4 ppm |

EXAMPLES 13–14: TWO TREATMENTS, AERATION IN SECOND, VARYING AMOUNT OF 1-CHLORO-2,6-DINITRO-4-(TRIFLUOROMETHYL)BENZENE

Two experiments were carried out to determine the effect of varying the ratio of 1-chloro-2,6-dinitro-4-(trifluoromethyl)benzene to sodium carbonate.

Each experiment was carried out as follows.

Sodium carbonate (12.0 grams) was dissolved in 95 ml of water and heated to 70° C. with agitation. The specified amount of 1-chloro-2,6-dinitro-4-(trifluoromethyl)-benzene, at a temperature of about 70° C., was added and the mixture agitated vigorously at about 70° C. for 30 minutes. The 1-chloro-2,6-dinitro-4-(trifluoromethyl)benzene was then separated.

Sodium carbonate (2.4 grams) was dissolved in 95 ml of water and heated to 70° C. with agitation. A specified amount of the 1-chloro-2,6-dinitro-4-(trifluoromethyl)-benzene from the first procedure, at a temperature of about 70° C., was added, and the mixture aerated with stirring at about 70° C. for 1 hour. The 1-chloro-2,6-dinitro-4-(trifluoromethyl)benzene was then separated.

The product from each procedure was aminated with di-n-propylamine, yielding N,N-di-n-propyl-2,6-dinitro-4-(trifluoromethyl)aniline which was analyzed for N-nitroso-N,N-di-n-propylamine. The results were as follows:

| Amount of 1-chloro-2,6-dinitro-4-(trifluoromethyl)-benzene employed in each of the two treatments | Concentration of N-Nitroso-N,N-di-n-propylamine |
| --- | --- |
| 138 grams | 1 ppm |
| 209 grams | 4 ppm |

EXAMPLES 15-17: TWO TREATMENTS, AERATION IN SECOND, PH DETERMINATIONS

A series of three experiments was carried out, varying the amount of sodium carbonate in the first treatment and with pH determinations made on the aqueous layers at the end of each treatment.

In each experiment, 175 grams of 1-chloro-2,6-dinitro-4-(trifluoromethyl)benzene, at a temperature of about 70° C., was added to a solution of sodium carbonate in 121 ml of water. The mixture was maintained at 70° C. for thirty minutes, then permitted to separate into layers and the pH of the aqueous layer taken. In the second treatment, the 1-chloro-2,6-dinitro-4-(trifluoromethyl)benzene from the first treatment, at a temperature of about 70° C., was added to a solution of 3 grams of sodium carbonate in 121 ml of water. The mixture was maintained at 70° C. for 1 hour with aeration, then permitted to separate into layers and the pH of the aqueous layer taken.

Each lot of 1-chloro-2,6-dinitro-4-(trifluoromethyl)benzene was aminated with di-n-propylamine and the ensuing N,N-di-n-propyl-2,6-dinitro-4-(trifluoromethyl)-aniline analyzed for N-nitroso-N,N-di-n-propylamine. The results were as follows:

| Amount of Sodium Carbonate in first treatment | pH of aqueous layer after: first treatment | second treatment | Concentration of N-nitroso-N,N-di-n-propylamine |
| --- | --- | --- | --- |
| 15.1 grams | 8.7 | 11 | 2 ppm |
| 9.1 grams | 8 | 11 | 3 ppm |
| 9.1 grams | 8 | 11 | 2 ppm |

EXAMPLES 18-20: TWO TREATMENTS, AERATION IN SECOND, VARYING IDENTITY OF BASE

A series of four experiments was carried out, varying the base.

Each experiment was carried out in accordance with the following procedures. Water (400 ml), or a solution of a selected base in 400 ml of water, was heated to 65°-70° C. 1-Chloro-2,6-dinitro-4-(trifluoromethyl)benzene (579 grams), at a temperature of about 70° C., was added and the mixture was stirred for 30 minutes at 65°-70° C. The mixture was permitted to seperate into layers, and the pH of the aqueous layer determined.

A solution of the same base in water (400 ml) was heated to 65°-70° C. 1-Chloro-2,6-dinitro-4-(trifluoromethyl)-benzene from the prior treatment, at a temperature of about 70° C., was added and the mixture was stirred for 1 hour at 65°-70° C. while air was sparged through the mixture. The mixture was permitted to separate into layers, and the pH of the aqueous layer determined.

A portion of the 1-chloro-2,6-dinitro-4-(trifluoromethyl)benzene from each treatment was aminated with di-n-propylamine and the ensuing N,N-di-n-propyl-2,6-dinitro-4-(trifluoromethyl)aniline analyzed for N-nitroso-N,N-di-n-propylamine. The results were as follows:

| Base | Amount of Base first treatment | second treatment | Concentration of N-nitroso N,N-di-n-propylamine | pH of aqueous layer at end of: first treatment | second treatment |
| --- | --- | --- | --- | --- | --- |
| -(control) | — | — | 75.8 ppm | — | — |
| Sodium carbonate | 50 g | 10 g | 3.1 ppm | 9.7 | 10.8 |
| Potassium carbonate | 65.3 g | 12.9 g | 2.9 ppm | 9.7 | 10.6 |
| Sodium hydroxide | 18.9 g | 3.8 g | 1.4 ppm | 11.9 | 11.2 |

EXAMPLES 21-22: TWO TREATMENTS, AERATION IN SECOND, EFFECT OF SODIUM CARBONATE IN SECOND

Two experiments were conducted in which only the second treatment step was varied — in one experiment, conducted in triplicate, the second treatment included sodium carbonate; in the second experiment, also conducted in triplicate, the second treatment was carried out without sodium carbonate present.

Sodium carbonate (15.1 grams) was dissolved in water (121 ml) and the solution heated to 70° C. with agitation. 1-Chloro-2,6-dinitro-4-(trifluoromethyl)benzene (175 grams), at a temperature of about 70° C., was added and the mixture maintained at 70° C. with agitation for 30 minutes. The 1-chloro-2,6-dinitro-4-(trifluoromethyl)benzene was then separated.

A solution of sodium carbonate (3 grams) in water (121 ml) (in the first experiment) or water alone (121 ml) (in the second experiment) was heated to 70° C. 1-Chloro-2,6-dinitro-4-(trifluoromethyl)benzene from the prior procedure was added and the mixture maintained at 70° C., with aeration, for one hour. The 1-chloro-2,6-dinitro-4-(trifluoromethyl)-benzene was then separated.

Each of the two treated lots of 1-chloro-2,6-dinitro-4-(trifluoromethyl)benzene was subsequently aminated with di-n-propylamine and the N,N-di-n-propyl-2,6-dinitro-4-(trifluoromethyl)aniline product analyzed for N-nitroso-N,N-di-n-propylamine. The results were as follows.

| Second Treatment | Concentration of N-nitroso-N,N-di-n-propylamine | | |
| --- | --- | --- | --- |
| Sodium carbonate added | 2 ppm, | <0.5 ppm, | 2 ppm |
| No sodium carbonate | 6 ppm, | 1 ppm, | <0.5 ppm |

EXAMPLES 23-25: SINGLE SIMULTANEOUS TREATMENT VS. TWO TREATMENTS WITH AERATION IN SECOND

A series of experiments was conducted to compare a single, simultaneous treatment with two treatments, with sodium carbonate in both but aeration only in the second treatment. The experiments were conducted in triplicate.

The two-treatment experiments were carried out essentially as follows. 1-Chloro-2,6-dinitro-4-(trifluoromethyl)benzene (175 grams), at a temperature of about 70° C., was added to a solution of sodium carbonate (15.1 grams) in water (121 ml) at 70° C. The mixture was maintained at 70° C. for 30 minutes, and the 1-chloro-2,6-dinitro-4-(trifluoromethyl)benzene then separated and added to another solution of sodium carbonate (3 grams) in water (121 ml) at about 70° C. This second mixture was held at 70° C. with aeration for 1 hour, then permitted to separate.

The single treatment experiments were carried out essentially as follows. 1-Chloro-2,6-dinitro-4-(trifluoromethyl)benzene (175 grams), at a temperature of about 70° C., was added to a solution of sodium carbonate (15.1 grams) in water (121 ml) at 70° C. The mixture was held at 70° C. with aeration for one hour, and the 1-chloro-2,6-dinitro-4-(trifluoromethyl)benzene then separated.

Each lot of 1-chloro-2,6-dinitro-4-(trifluoromethyl)benzene was aminated with di-n-propylamine and the N,N-di-n-propyl-2,6-dinitro-4-(trifluoromethyl)aniline product analyzed for N-nitroso-N,N-di-n-propylamine. The results were as follows.

| Treatment | Concentration of N-nitroso-N,N-di-n-propylamine |
|---|---|
| —(control, no treatment) | 120 ppm |
| Single treatment | 5 ppm |
|  | 1 ppm |
|  | 2 ppm |
| Two treatments | 1 ppm |
|  | 1 ppm |
|  | <0.5 ppm |

EXAMPLES 26–30: SINGLE SIMULTANEOUS TREATMENT, EFFECT OF AIR FLOW RATE

A series of five experiments was carried out to determine the effect of the flow rate of the gas, which was air.

Each experiment was conducted as follows. A sample of 1-chloro-2,6-dinitro-4-(trifluoromethyl)benzene (34.7 grams) was heated to about 70° C. and added to a slurry of sodium carbonate (7.4 grams) in water (24 ml). The mixture was heated to 70° C. and air was bubbled through, at various rates in four of the experiments. The fifth experiment was conducted without any air, to serve as a control. Treatment time was 30 minutes.

Without separation (except in one of the experiments), the treated 1-chloro-2,6-dinitro-4-(trifluoromethyl)benzene was aminated with di-n-propylamine. The N,N-di-n-propyl-2,6-dinitro-4-(trifluoromethyl)aniline products were analyzed for N-nitroso-N,N-di-n-propylamine. The results were as

| Treatment | Concentration of N-nitroso-N,N-di-n-propylamine |
|---|---|
| no aeration (control) | 21 ppm |
| aeration, amination without separation: |  |
| 450 ml/min | 5.8 ppm |
| 300 ml/min | 7.7 ppm |
| 170 ml/min | 11.7 ppm |
| aeration at 450 ml/min, amination after separation | 1.4 ppm |

We claim:

1. A process for lowering the concentration of nitrosating agents in 1-chloro-2,6-dinitro-4-(trifluoromethyl)benzene which comprises
   (1) bubbling a gas which is non-reactive with 1-chloro-2,6-dinitro-4-(trifluoromethyl)benzene through a mixture of (a) 1-chloro-2,6-dinitro-4-(trifluoromethyl)benzene containing nitrosating agents and (b) an aqueous solution of a base which is
      (a) sodium carbonate,
      (b) potassium carbonate,
      (c) sodium hydroxide, or
      (d) potassium hydroxide,
   at a temperature of about 50°–100° C., until the concentration of nitrosating agents is lowered; or
   (2) contacting 1-chloro-2,6-dinitro-4-(trifluoromethyl)benzene containing nitrosating agents with an aqueous solution of a base which is
      (a) sodium carbonate,
      (b) potassium carbonate,
      (c) sodium hydroxide, or
      (d) potassium hydroxide,
   at a temperature of about 50°–100° C., separating the once-treated 1-chloro-2,6-dinitro-4-(trifluoromethyl)benzene, and thereafter bubbling a gas which is non-reactive with 1-chloro-2,6-dinitro-4-(trifluoromethyl)benzene through an aqueous mixture of the once-treated 1-chloro-2,6-dinitro-4-(trifluoromethyl)-benzene, at a temperature of 50°–100° C., whereby there is obtained 1-chloro-2,6-dinitro-4-(trifluoromethyl)benzene characterized by a lowered concentration of nitrosating agents.

2. The process of claim 1 carried out as described in paragraph (1) of said claim.

3. The process of claim 2 wherein the treated 1-chloro-2,6-dinitro-4-(trifluoromethyl)benzene is thereafter separated.

4. The process of claim 3 wherein
   (1) the base is sodium carbonate,
   (2) the gas is air, and
   (3) the temperature is 60°–70° C.

5. The process of claim 1 carried out as described in paragraph (2) of said claim.

6. The process of claim 5 wherein the aqueous mixture of the once-treated 1-chloro-2,6-dinitro-4-(trifluoromethyl)benzene includes a base which is
   (a) sodium carbonate,
   (b) potassium carbonate,
   (c) sodium hydroxide, or
   (d) potassium hydroxide.

7. The process of claim 6 wherein the treated 1-chloro-2,6-dinitro-4-(trifluoromethyl)benzene is thereafter separated.

8. The process of claim 7 wherein
   (1) the base in each treatment is sodium carbonate,
   (2) the gas is air, and
   (3) each treatment is conducted at a temperature of 60°–70° C.

9. A process for lowering the concentration of nitrosating agents in 1-chloro-2,6-dinitro-4-(trifluoromethyl)benzene which comprises
   (1) in a first treatment, contacting 1-chloro-2,6-dinitro-4-(trifluoromethyl)benzene containing nitrosating agents with an aqueous solution of a base which is
      (a) sodium carbonate,
      (b) potassium carbonate,
      (c) sodium hydroxide, or
      (d) potassium hydroxide,
   at a temperature of about 50°–100° C., and
   (2) separating the once-treated 1-chloro-2,6-dinitro-4-(trifluoromethyl)benzene,
   (3) in a second treatment, bubbling a gas which is non-reactive with 1-chloro-2,6-dinitro-4-(trifluoromethyl)benzene through a mixture of (a) the once-treated 1-chloro-2,6-dinitro-4-(trifluoromethyl)benzene and (2) an aqueous solution of a base which is
(a) sodium carbonate,
(b) potassium carbonate,
(c) sodium hydroxide, or
(d) potassium hydroxide, at a temperature of about 50°–100° C., and separating 1-chloro-2,6-dinitro-4-(trifluoromethyl)benzene characterized by a lowered concentration of nitrosating agents.

10. The process of claim 9 wherein
(1) the base in each treatment is sodium carbonate,
(2) each treatment is conducted at a temperature of 60°–70° C., and
(3) the gas is air.

* * * * *